United States Patent [19]

Parker

[11] Patent Number: 5,254,761
[45] Date of Patent: Oct. 19, 1993

[54] PROCESS FOR SELECTIVE REDUCTION OF UNSATURATED ORGANIC COMPOUNDS

[75] Inventor: Dane K. Parker, Massillon, Ohio

[73] Assignee: The Goodyear Tire & Rubber Company, Akron, Ohio

[21] Appl. No.: 885,082

[22] Filed: May 18, 1992

[51] Int. Cl.$^5$ .............. C07C 5/00; C07C 5/02; C07C 5/04; C07C 2/00

[52] U.S. Cl. .................. 585/250; 585/271; 585/275; 585/700

[58] Field of Search ............ 585/250, 271, 275, 700

[56] References Cited

U.S. PATENT DOCUMENTS

| | | | |
|---|---|---|---|
| 4,452,950 | 5/1984 | Wideman | 525/339 |
| 4,469,849 | 9/1984 | Murrer et al. | |
| 5,039,737 | 8/1991 | Parker et al. | 524/804 |

OTHER PUBLICATIONS

Hunig et al., "The Chemistry of Diimine", *Angewandte Chemie*, International Edition, vol. 4, No. 4, Apr. 1965, pp. 271–280.

*Organic Syntheses*, Collective Volume V, H. E. Baumgarten, ed.; Pub. by John Wiley & Sons, New York, 1973; pp. 281–284.

*Organic Reactions*, vol. 40, L. A. Paquette et al, ed: Pub. by John Wiley & Sons, New York, 1991; pp. 91–155.

D. K. Parker et al, "A New Process for the Preparation of Highly Saturated Nitrile LRubber in Latex Form: (Chemistat"), paper No. 58, presented at the 139th meeting of the Rubber Division, American Chemical Society, Toronto, Ontario, Canada, May 21–24, 1991 (33 pages).

*Primary Examiner*—Anthony McFarlane
*Assistant Examiner*—Nhat D. Phan
*Attorney, Agent, or Firm*—Alvin T. Rockhill; Louis F. Kreek, Jr.

[57] ABSTRACT

A reducible unsaturated organic compound is reduced with diimide in an aqueous emulsion comprised of water, an organic phase which contains the compound to be reduced, and an effective stabilizing amount of an anionic surfactant. The organic compound is preferably an unsaturated organic compound containing a carbon-to-carbon multiple bond, which is preferably a carbon-to-carbon double bond. Diimide is formed by reaction of hydrazine with an oxidant in the aqueous emulsion described above. The preferred oxidant is hydrogen peroxide. A product is obtained in high yield and purity in most cases. This process is especially useful for the selective reduction of a compound having two or more carbon-to-carbon double bonds of different reactivities or a carbon-to-carbon double bond and a functionality (e.g., an O—O or S—S linkage) which is reducible by catalytic hydrogenation but not diimide.

14 Claims, No Drawings

PROCESS FOR SELECTIVE REDUCTION OF UNSATURATED ORGANIC COMPOUNDS

This invention relates to processes for reduction of carbon to carbon double bonds in unsaturated organic compounds and in particular to a process for the selective reduction of an unsaturated organic compound with diimide in an aqueous anionic emulsified medium.

BACKGROUND ART

It is known that rubber latexes, especially nitrile-butadiene rubber (NBR) latexes can be directly reduced in the latex form to the saturated analog (HNBR) in the presence of hydrazine, an oxidizing agent and a metal ion initiator. Such reaction is disclosed in U.S. Pat. No. 4,452,950 to Wideman. Even with large excesses of hydrazine, reductions are not quantitative and there is a wide range, from 20% to 83% olefinic reduction, in the examples given. This patent states that the polymer be prepared in an aqueous emulsion polymerization and be reduced in the latex form without prior coagulation or use of organic solvents. Use of a surfactant in emulsion polymerization is standard procedure and it is believed that an anionic surfactant as used, even though surfactant is not mentioned. This patent and the instant application are commonly assigned.

Hunig et al "The Chemistry of Diimide", *Angewandte Chemie*. International Edition, vol. 4, no. 4, April, 1965, pps. 271-280, describes methods for generating diimide (which this reference refers to as diimine) and to reactions of diimide with compounds containing one or more carbon-to-carbon double bond. Also described are decomposition of one mole of diimide into nitrogen and hydrogen, and disproportionation of two moles of diimide into nitrogen and hydrazine (these are competing reactions, as disclosed in the reference). Substrate specificity of hydrogenation, (i.e. multiple bonds which do not react with diimide) and competition between olefin hydrogenation, and between disproportionation and olefin hydrogenation, are also described. Reactions described were carried out in solution.

*Organic Syntheses*, collective vol. V, H. E. Baumgarten, Editor, John Wiley & Sons, Inc. 1973, pp 281-290, describes reduction of cis,trans,trans-1,5,9-cyclododecatriene to cis-cyclododecene with hydrazine and air in an ethanol solution containing copper sulfate. Product recovery includes filtration, extraction of the filtrate with petroleum ether, and distillation. A yield of 64-80 percent and a purity of about 80-90 percent are reported.

*Organic Reactions*, vol. 40, L. A. Paquette et al., Editors, John Wiley & Sons, Inc. 1991, pp 91-155, is a compilation of previously published procedures for generation of diimide and for reaction of diimide with compounds containing a carbon-to-carbon double bond. Relative reactivity of double bonds, stereoselectivity, and groups (such as N—O) which can be reduced with other reducing agents but not with diimide, are also noted. This article contains a number of specific experimental procedures, (all taken from earlier published literature) showing reduction of various substrate compounds containing carbon-to-carbon double bonds with diimide. Reduction of a number of additional substrate compounds is shown in tables. Reactions are carried out in solution, using organic solvents for the most part. The reference notes the need to use large excesses of diimide, owing to disproportionation and other side reactions.

DISCLOSURE OF THE INVENTION

This invention provides a process for reducing one or more carbon-to-carbon double bonds in an unsaturated organic compound containing the same, which comprises contacting the unsaturated organic compound with a diimide reducing agent in an anionically emulsified aqueous medium and in the presence of an oxidant and a metal oxide initiator.

The preferred diimide reducing agent is hydrazine or a hydrazine hydrate.

Reduction according to this invention is selective. Allylic and benzylic functions do not undergo a hydrogenolysis with the diimide, nor are sensitive hetero atom bonds such as N—N, N—O, O—O, S—S or C-halogen destroyed.

The present invention more specifically reveals a process for reducing a reducible carbon-to-carbon multiple bond in an unsaturated organic compound containing the same which comprises contacting said organic compound with hydrazine or a hydrate thereof and an oxidant in an emulsion comprising water, an effective amount of a metal ion initiator, a water immiscible organic phase containing said organic compound, and an effective stabilizing amount of an anionic surfactant.

DETAILED DESCRIPTION

The starting material (or substrate) is an unsaturated organic compound having one or more carbon-to-carbon double bonds, or alternatively one or more carbon-to-carbon triple bonds (or both). The organic compound may be either acyclic, carbocyclic or heterocyclic. The compound is a monomer (whether or not capable of homopolymerization) as opposed to a dimer, oligomer or polymer. The compound may have functionalities which are reducible by means other than the oxidant/reducing agent combination herein; in fact, one of the important advantages of the present process is that it gives a clean and (in most cases) quantitative or nearly quantitative reduction of non-aromatic carbon-to-carbon unsaturations while leaving certain other groups untouched. The molecular weight of the starting organic compound is typically no more than 1000 and generally no more than 500. Additionally, the organic compound does not contain any repeating monomeric units.

Allylic and benzylic functions do not undergo cleavage reactions with diimide according to this invention. Similarly, hetero atom bonds such as N—N, N—O, and O—O, which often suffer reductive cleavage under catalytic hydrogenation conditions, remain intact during diimide reduction according to this invention. Therefore, the process of this invention is especially well suited to reduction of carbon-to-carbon double or triple bonds in compounds which also contain any of these functionalities.

Functionalities which are susceptible to reduction by other means but resistant or inert to attack by diimide are known in the art, as illustrated for example in the non-patent literature references cited earlier herein. Functionalities which are inert to diimide in solution are also inert to diimide in emulsion reaction procedures according to this invention.

It is also known in the art, as illustrated in the non-patent literature cited earlier herein, that certain carbon-to-carbon double bonds are more reactive than others. Selective reduction of the more reactive double bond is facile in emulsion in accordance with this invention. On the other hand, selective reductions with diimide in solution are difficult, as noted in *Organic Reactions,* cited supra at page 96, owing to the need to use large excesses of diimide.

The reducing agent of this invention is diimide, $N_2H_2$, which may be formed in situ as will be described hereinafter. Diimide has three isomeric forms, i.e., cis-diimide, trans-diimide and 1,1-diimide as described in *Organic Reactions,* cited supra, at pages 92 and 93.

Various reagents and reagent combinations which will generate diimide in situ are disclosed in "Organic Reactions" on pages 99 and 100. A preferred reagent combination is the combination of hydrazine and an oxidizing agent (or oxidant) and in particular a combination of molecular oxygen (e.g., air) or a peroxide (especially hydrogen peroxide) and hydrazine. The term "hydrazine", will be used herein to denote anhydrous hydrazine and the hydrates, of which the monohydrate is the most common.

The oxidizing agent may be either molecular oxygen (air or oxygen enriched air or pure oxygen), hydrogen peroxide (which may be an aqueous solution), or an organic hydroperoxide. Representative hydroperoxides are cumyl hydroperoxide, t-butyl hydroperoxide and p-menthane hydroperoxide. Other commercially available oxidants that are known to oxidize hydrazine include iodine, iodate ion, hypochlorite ion, ferricyanide ion and the like. The classes of oxidants disclosed herein are essentially the same as those disclosed in U.S. Pat. No. 4,452,950 cited supra. A common characteristic shared by molecular oxygen, hydrogen peroxide and the hydroperoxides is that all have an O—O bond.

When the oxidant is either molecular oxygen or hydrogen peroxide, a metal initiator, which may be either a metal ion or a metal salt, is required. Suitable metal initiators are disclosed in U.S. Pat. No. 4,452,950. Representative metals whose ions or salts will react with hydrazine and are, therefore, useful in the present invention are as follows:

| | | |
|---|---|---|
| Antimony | Arsenic | Bismuth |
| Cerium | Chromium | Cobalt |
| Copper | Gold | Iron |
| Lead | Manganese | Mercury |
| Molybdenum | Nickel | Osmium |
| Palladium | Platinum | Polonium |
| Selenium | Silver | Tellurium |
| Tin | Vanadium | |

The copper ion is a particularly useful metal initiator, and is conveniently supplied in the form of aqueous copper sulfate. The concentration of metal ion initiator is not critical and usually only very small amounts are required. Reduction according to this invention is carried out in an emulsion which comprises an aqueous phase and an organic phase. The aqueous phase, which is the continuous phase, comprises water, an anionic surfactant (to be described below), and a metal initiator (described above). The organic phase contains the organic substrate compound to be reduced, and in many cases, the substrate is the sole constituent of the organic phase, other than the hydrophobic moiety (moieties) of the surfactant(s). Essential to the success of the present process is the presence of an anionic surfactant in the aqueous medium. Commercially available anionic surfactants may be used. A preferred anionic surfactant is "Dowfax" 2A1, which is a branched $C_{12}$ alkylated diphenyloxide disulfonic acid disodium salt. Other classes of suitable anionic surfactants include the following:

Alkylaryl Sulfonates: "Witconate ™" LX Flakes—(Witco Corp.) and "Siponate" DDB-40—(Rhone-Poulenc).

Sulfonated Amines and Amides: "Emlcupon" L—(Emkay Chemical Company) and "Indulin" MQK—(Westvaco Corp.).

Amphoteric Betaine Derivatives: "Alkateric ™" CB—(Rhone - Poulenc) and "Schercotaine" MAB—(Scher Chemicals, Inc.).

Diphenyl Sulfonate Derivatives: "Dowfax" 2A1—(Dow Chemical Company) and "Poly-Tergent" 2A—(Olin Corporation).

Ethoxylated Fatty Acids: "Chemax" ML—(Chemax, Inc.) and "Hodag L"—(Hodag Chemical Corporation).

Olefin Sulfonates: "Bio-Terge" AS-40—(Stepan Company) and "Siponate" A246L—Rhone - Poulenc).

Sulfates and Sulfonates of Ethoxylated Alkyl Phenols: "Aerosol" NPES—(American Cyanamid) and "Polystep" F-2—(Stepan Company)

Sulfates and Sulfonates of Oils and Fatty Acids: "Dymsols"—(Henkel Corporation) and "Eureka" 102—(Atlas Refinery, Inc.)

Sulfates: "Duponol" QC—(DuPont) and "Sandoz Sulfate"—(Sandoz Chemical Corporation)

Sulfates of Ethoxylated Alcohols: "Texapon" AS-V—(Henkel Corporation) and "Carsonol ®" SES-A—(Lonza, Inc.)

Sulfates of Fatty Esters: "Emkafol"—(Emkay Chemical Company) and "Sulfonated GTO"—(National Starch & Chemical).

Sulfonates of Condensed Naphthalenes: "Erional ®"—(Ciba-Geigy Corporation) and "Harol" RG—(Graden Chemical).

Sulfosuccinates and Derivatives: "Aerosol" OT—(American Cyanamid) and "Incrosul" LTS—(Croda, Inc.).

Sulfosuccinamates: "Aerosol" 22—(American Cyanamid) and "Octosol" A-1—(Textile Rubber & Chemical Company).

Sulfonates of Dodecyl and Tridecylbezenes: "Bio-Soft" N-300—(Stepan Company) and "Witconate ™" 60B—(witco Corporation).

As is true generally of surfactants, the surfactants herein have a hydrophilic moiety and a hydrophobic moiety.

An effective stabilizing amount of the anionic surfactant is used. The term, "effective stabilizing amount" denotes an amount of surfactant sufficient to maintain a stable aqueous emulsion. As those skilled in the art will recognize, most or nearly all of the unsaturated organic compounds which are reducible in accordance with this invention are immiscible in water. The amount of surfactant is not critical and is typically from about 0.5 to about 15 parts by weight per 100 parts of organics.

The amount of surfactant required may be determined empirically for each system.

Use of a stabilizing amount of an anionic surfactant is essential to the success of the present process. Similar results are not obtained with a cationic surfactant or a nonionic surfactant.

A mildly alkaline medium, e.g. one having a pH from about 8 to about 12 is used to carry out reduction according to this invention. The pH will usually and preferably be in the range of 9.5 to 10.5.

In some cases it may be desirable to use an organic co-solvent, for instance, when the substrate is a solid. The co-solvent should have low water miscibility and be unreactive toward hydrazine and oxidants. Suitable co-solvents include toluene, xylene, hexane and heptane. The purpose of a co-solvent is to dissolve non-liquid (solid) substrates and aid in their emulsification. The amount of co-solvent (when used) may range from about 0.5 to about 10,000 parts by weight per 100 parts of unsaturated carbon compound. The actual amount of co-solvent required is dependent on the solubility of the substrate in the chosen solvent.

Reduction of double or triple bonds in unsaturated organic compounds in accordance with the present invention is essentially quantitative or nearly quantitative when carried out in an emulsified aqueous/organic medium in accordance with this invention. In addition, reduction efficiency based on hydrogen peroxide consumed, approaches theoretical quantity (1 mole of double bond reduced for each mole of hydrogen peroxide consumed). In nearly all cases, reduction efficiency is at least about 80 percent and in most cases is at least about 85 percent. (A reduction efficiency of 85 percent represents 0.85 mole of reduction product for each mole of hydrogen peroxide consumed). In short, side reactions occur to a remarkably small extent. Conversion of the starting material or substrate to desired reduction product (or products) is usually nearly quantitative. Analysis of the reaction product typically shows that nearly all of the starting material can be accounted for, either as one or more reduction products or unreacted starting material. This is in marked contrast to earlier known processes, including those described in "Organic Reactions" (published 1991) and other prior art references, wherein reduction is carried out in solution and an excess, and usually a substantial excess, of hydrazine and oxidant (or other reagent or reagent combination yielding diimide) is required. In fact, results in this regard are as good as, or even better than, the results in reducing >C=C< double bonds in rubber latexes, as described in U.S. Pat. No. 4,452,950 cited supra.

Furthermore, quantitative or nearly quantitative reduction of carbon-to-carbon multiple bonds is obtained according to the present invention without regard to the hydrazine concentration in the preferred reaction system. Prior art process in which a hydrazine/oxidant combination is used, become less efficient, with a proportionately greater amount of side reactions taking place, as the diimide concentration increases. This means that the prior art processes must generate very low concentrations of diimide in order to achieve reduction without undue side reactions taking place.

No one prior to the present invention has applied the emulsion reduction technique as described herein to the reduction of unsaturated organic compounds, as far as applicant is aware even through U.S. Pat. No. 4,452,950 (relating to reduction of double bonds in rubber latexes formed by emulsion polymerization) was issued in 1984. Attention is called to "Organic Synthesis" (1991) cited supra in this regard. The unsaturated polymer latex systems described in U.S. Pat. No. 4,452,950 include an anionic surfactant, even though such surfactant is not specifically mentioned.

While applicant does not wish to be bound by any theory of reaction or by any explanation as to why outstanding results are obtained according to the present invention, in contrast to the poor results previously obtained when reducing unsaturated organic compounds, applicant believes that the most probable explanation is that given below.

Hydrazine reacts with an oxidizing agent or oxidant, e.g., molecular oxygen or hydrogen peroxide to yield diimide (referred to diimine by some authors) according to equation (1) below.

$$H_2N-NH_2 + [O] \rightarrow [HN=NH] \tag{1}$$

When the oxidant is hydrogen peroxide, the formation of diimide may be represented by equation (1a) below.

$$H_2N-NH_2 + H_2O_2 \rightarrow [HN=NH] + 2H_2O \tag{1a}$$

The resulting diimide, which is an unstable intermediate and therefore bracketed in equation (1), then reacts with a carbon-to-carbon double bond according to equation (2).

$$HN=NH + >C=C< \rightarrow N_2 + >CH-CH< \tag{2}$$

Acetylenic compounds, i.e., compounds having a carbon-to-carbon triple bond, react in an analogous manner except that stepwise reduction is possible. Two moles of reducing agent per mole of acetylenic compound accomplish a complete reduction of the triple bond to a single bond. One mole of reducing agent per mole of acetylenic compound reduces the triple bond to a double bond.

Side reactions may occur to a limited extent. The principal side reaction is the bi-molecular disproportionation according to equation (5) below, with the monomolecular decomposition shown in equation (4) being relatively minor.

$$HN=NH \rightarrow N_2 + H_2 \tag{4}$$

$$2HN=NH \rightarrow N_2 + H_2N-NH_2 \tag{5}$$

Reaction (5) is the main competing reaction to the process shown in equation (2). The rate of the disproportionation reaction (5) in homogeneous solutions increases with the square of the diimide concentration whereas the rate of reaction (2) (olefin hydrogenation) increases with the first power of the diimide concentration. Therefore, the yield of the hydrogenated product will be reduced under all conditions leading to an increase in the diimide concentration. Applicant finds remarkably that this is not the case with the anionically emulsified reaction systems of this invention. While applicant does not wish to be bound by any theory of reaction, a possible and even probable explanation is given below.

When a molecule of unsaturated organic compound collides with a diimide molecule, a carbon-to-carbon bond in the unsaturated compound will be reduced in accordance with equation (2) above. (An analogous reaction will take place if the carbon-to-carbon bond is a triple bond instead of a double bond as shown). If on the other hand one diimide molecule collides with another diimide molecule, reaction (5) takes place and diimide is consumed without any useful reduction of a carbon-to-carbon bond. It is known that emulsified systems create a multiplicity of microscopic particles, typically from about 30 to about 5000 nanometers (nm) in diameter. Each such particle of unsaturated organic compound is believed to function like an individual reactor which is isolated from all of the other individual particles or "reactors" in the system. This greatly increases the probability of reaction of a diimide molecule with a molecule of unsaturated organic compound in accordance with equation (2) and correspondingly decreases the probability and extent of side reaction (5).

This invention will now be described further with reference to the specific examples which follow.

EXAMPLE I

Diimide reduction of cis,trans,trans-1,5,9-cyclododecatriene (I) in emulsion

The title reduction may be depicted by the equation below:

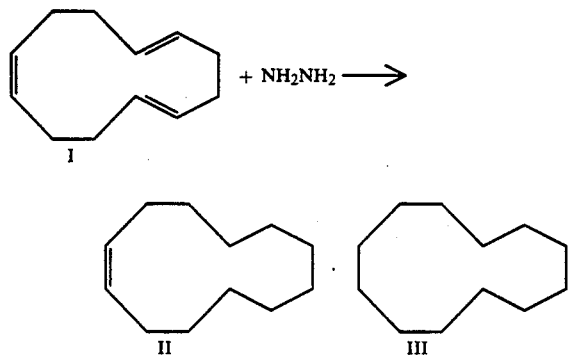

Reactants include hydrazine and hydrogen peroxide in addition to cis,trans,trans-1,5,9-cyclododecatriene (I), which is shown.

PART A: Preparation of Cyclododecatriene Emulsion

A 600 mL beaker was charged with 150 g deionized water, 100 g of 91% pure 1,5,9-cyclododecatriene and 5.0 g of stearic acid. The resulting mixture was heated to 75°–80° C. to melt stearic acid and was intensively mixed at this temperature using a high shear Tekmar agitator while adding sufficient 50% aq. KOH to raise the pH to 10.5–11.0. The emulsion was cooled to room temperature and allowed to stand overnight. (Note: density differences between bulk water and emulsified particles caused some separation overnight, but gentle mixing again gave a uniform emulsion). The final emulsion contained 39.2 percent 1,5,9-cyclododecatriene (I) by weight.

PART B: Diimide Reduction

Into a 250 mL neck round bottom flask, equipped with a mechanical stirrer, thermometer, heating mantle and feeding tube for hydrogen peroxide, the following were charged in the order named:

(a) 76.53 g of 1,5,9-cyclododecatriene emulsion (ca. 0.1685 moles of cyclododecatriene or 0.5057 moles of double bonds).

(b) 2 ml of copper sulfate pentahydrate/"Dowfax" 2A1 solution, prepared by dissolving 0.385 g (0.00154 moles) of copper sulfate pentahydrate, 7.5 g (ca. 0.00592 mols) of 45 percent active "Dowfax" 2A1 (which is a branched $C_{12}$ alkylated diphenyloxide disulfonic acid disodium salt) in 92 mL of tap water.

(c) 27.55 g of 64 percent aqueous hydrazine (0.5544 moles).

Then 57.12 g of 33 percent aqueous hydrogen peroxide (0.5544 moles) was slowly added dropwise over several hours at a rate sufficient to keep the reaction temperature between 60° and 65° C. (Actually a total of 0.68 moles of hydrogen peroxide was added. The samples of the reaction mixture showed very little change in composition after 0.5544 moles was added). No defoamer was used and no foaming was observed during the run. Samples of the reaction mixture were analyzed periodically during the course of reaction as hydrogen peroxide was added.

TABLE 1 below shows the progress of diimide emulsion reduction of 1,5,9-cyclododecatriene (I) in accordance with Example 1 as hydrogen peroxide is added. As TABLE 1 shows, the reactant 1,5,9-cyclododecatriene (I) is steadily consumed as hydrogen peroxide is added, the quantity remaining reaching essentially 0 when about 0.53 moles (corresponding to about 95–96 percent of the theoretical quantity) of hydrogen peroxide had been added. Further addition of hydrogen peroxide causes little change in either the quantity of reactants still present or of the quantities of either product compound. The quantity of cyclododecene (II) goes through a maximum after approximately 0.24–0.34 moles of hydrogen peroxide have been added and thereafter decreases as more cyclododecane (III) is formed. Percentage conversion shown in TABLE 1 are GC (gas chromatography) area percentages. From the GC results shown in TABLE 1, it is estimated that a total of 0.4825 moles of double bonds were reduced out of the original 0.5057 moles present (95% reduction) with 87 percent of the product being cyclododecane (III) and 12.6 percent being cyclododecene (II). This represents a hydrazine consumption ratio of about 1.15, i.e., about 1.15 moles of hydrazine consumed per mole of double bonds converted. This is arrived at as follows: 0.5544 moles hydrazine/0.4825 of double bonds converted = 1.15. The double bond reduction efficiency which is the reciprocal of the hydrazine conversion ratio, is about 87 percent.

TABLE 1

Diimide emulsion reduction of 1,5,9-Cyclododecatriene (I)

| Moles H$_2$O$_2$ added | Reaction mixture | | |
|---|---|---|---|
| | Mole % I (substrate) | Mole % II (product) | Mole % III (product) |
| .05 | 84 | 16 | trace |
| .10 | 68 | 29 | 3 |
| .15 | 54 | 38 | 8 |
| .20 | 44 | 43 | 11 |
| .25 | 35 | 47 | 17 |
| .34 | 21 | 48 | 31 |
| .44 | 8 | 40 | 51 |
| .48 | 5 | 34 | 60 |
| .53 | 1 | 15 | 84 |
| .58 | 0 | 13 | 87 |
| .68 | 0 | 13 | 87 |

Note:
Compounds in TABLE 1 are as follows:
I = 1,5,9-cyclododecatriene (starting material)
II = cyclododecene (a product)
III = cyclododecane (the principal product)

EXAMPLE II

Diimide reduction of vinyl cyclohexene in emulsion
PART A. Preparation of Emulsion An emulsion of vinyl cyclohexene (IV) (100 g) was prepared in the same manner and using the same equipment as described in example I, part A, except that vinyl cyclohexene was substituted for 1,5,9-dodecatriene.

PART B. Diimide Reduction Procedure

Into a 250 mL 3 neck round bottom flask, equipped with a mechanical stirrer, thermometer, heating mantle and peroxide inlet tube, the following were charged in the order named:
(a) 69.78 g (0.2528 mols) of vinyl cyclohexene emulsion.
(b) 2 ml of copper sulfate/"Dowfax" 281 solution (same composition as in Example 1).
(c) 27.55 g (0.5544 moles) of hydrazine.

The above mixture was heated to 64° C. Over a seven hour period, 57.12 g (0.5544 moles) of 33 percent aqueous hydrogen peroxide was added dropwise at such rate as to keep the reaction temperature between 60° and 65° C. The reaction product was analyzed by gas chromatography (GC).

The amount of reaction product (designated as "Unknown I") increased nearly linearly and the amount of vinyl cyclohexene starting material decreased correspondingly nearly linearly as hydrogen peroxide was added.

The final product contained 40 percent by weight of "unknown I" and 60 percent of unreacted vinyl cyclohexene. While "Unknown I" was not analyzed and is therefore characterized as an unknown, it is believed that this compound is in fact ethyl cyclohexene. The fact that only one unknown was found in the product indicates that only one of the two double bonds in the starting vinyl cyclohexene was reactive under the conditions used; the other double bond (believed to the cyclic olefin, which did not effectively compete with the pendent vinyl double bond) was inert.

EXAMPLE III

Diimide reduction of 7-methyl-1,6-octadiene in emulsion.

PART A: Preparation of emulsion

An emulsion of 100 g of 7-methyl-1,6-octadiene was prepared in the manner described in Example 1, PART A, except that 7-methyl-1,6-octadiene was used instead of 1,5,9-cyclododecatriene.

PART B: Diimide reduction

The procedure of Example 1, Part B was followed except that 79.97 g of the emulsion prepared in part A (containing 0.2524 mols of 7-methyl-1,6-octadecadiene) was used in place of the emulsion described in Example 1.

Samples were taken and analyzed by GC during the course of hydrogen peroxide addition and when all hydrogen peroxide addition was complete. Amounts of product increased almost, but not quite linearly, and amounts of starting material correspondingly decreased almost but not quite linearly as hydrogen peroxide was added. The final product, as shown by GC analysis, contained about 78 percent of 2-methyl-2-octene and about 19 percent of unreacted starting material. Presence of only one reaction product and the high degree of accountability (about 97 percent) shows that only one of the two double bonds in the starting material was reactive, the other being inert.

EXAMPLE IV

Diimide reduction of dicyclopentadiene

PART A: Preparation of emulsion

An aqueous emulsion containing 100 g of 3a,4,7,7a-tetrahydro-4,7-methano-1H-indene (CAS registry no. 77-73-6, also known as "dicyclopentadiene") was prepared in the manner described in Example I, part A.

PART B: Diimide reduction

The procedure of Example I, part B, except that 85.26 g of the emulsion prepared in part A was used instead of the emulsion described in Example I. This emulsion contained 0.2527 moles of dicyclopentadiene.

Reaction product samples were analyzed periodically by GC as hydrogen peroxide was added and when hydrogen peroxide addition was complete.

The amount of starting material decreased almost linearly and the amount of "Unknown Number I" increased almost linearly until about 46 grams of hydrogen peroxide (representing about 88 percent of the theoretical amount required for reduction of both double bonds in the starting material) had been added. At this point the reaction mixture contained about 99 percent of "Unknown I", about 1 percent of "Unknown II" and substantially no starting material, as shown by GC analysis. When addition of hydrogen peroxide was complete, the reaction product contained about 88 percent of "Unknown I" and about 12 percent of "Unknown II" and substantially no starting material. It is believed that "Unknown I" is 3a,4,5,6,7,7a-hexahydro-4,7-methano-1H-indene (CAS no. 4488-57-7) and that "Unknown II" is 1,3,4,5,6-octahydro-4,7-methano-1H-indene (CAS no. 6004-38-2).

The foregoing examples are illustrative of the types of unsaturated compounds that can be reduced with diimide according to the present invention. These examples are not intended to be exhaustive. Suitable types of compounds which can be reduced according to the present invention have been described earlier in the specification.

The foregoing examples show that reduction of double bonds in aqueous emulsion with diimide according to the present invention is nearly quantitative (since the quantity of hydrogen peroxide was about 10 to at most 15 percent in excess of stoichiometric in the above examples) which is in marked contrast to the much poorer results obtained when reducing an unsaturated organic compound with diimide in solution. The examples also show that, in many cases, a compound containing two double bonds may be reduced selectively, only one of the double bonds being reduced while the other remains intact. Examples II, III, and IV illustrate this. Where such selectivity exists (and this has been discussed earlier in this specification) the present process affords a superior alternative to catalytic hydrogenation, in which all double bonds are reduced. Also, as noted earlier, certain diatom difunctionaltities (heteroatom bonds) such as N—N, N—O, and others noted earlier, are destroyed by catalytic hydrogenation but are inert to diimide reduction. All percentages are by weight unless expressly stated otherwise.

While this invention has been described in detail with particular reference to specific embodiments thereof, it shall be understood that such description is by way of illustration and not limitation.

What is claimed is:

1. A process for reducing a reducible carbon-to-carbon multiple bond in a water-immiscible unsaturated organic compound containing the same and having a molecular weight not over 1000 which comprises contacting said organic compound with hydrazine or a hydrate thereof and an oxidant selected from the group consisting of oxygen, hydrogen peroxide and organic hydroperoxides in an alkaline emulsion comprising an aqueous phase containing water and an effective amount of metal ion initiator, a water immiscible organic phase containing said organic compound, and an effective stabilizing amount of an anionic surfactant.

2. A process according to claim 1 wherein said carbon-to-carbon multiple bond is a carbon-to-carbon double bond.

3. A process according to claim 2 wherein said unsaturated organic compound contains more than one carbon-to-carbon double bond.

4. A process according to claim 3 wherein said double bonds have different reactivities whereby selective reduction of said unsaturated organic compound takes place.

5. A process according to claim 1 wherein the reaction is carried out at temperature from 0° C. to 100° C.

6. A process according to claim 5 wherein said temperature is from about 40° C. to about 80° C.

7. A process according to claim 6 wherein said temperature is from about 50° C. to about 75° C.

8. A process according to claim 5 wherein the PH of said emulsion is from 9.5 to 10.5.

9. A process according to claim 1 wherein the pH of said emulsion is from about 8 to about 12.

10. A process according to claim 1 wherein said oxidant is hydrogen peroxide.

11. A process according to claim 1 wherein the metal ion initiator is a water soluble copper salt.

12. A process according to claim 1 wherein the organic compound has a molecular weight not over 500.

13. A process according to claim 1 wherein said emulsion has a continuous phase and a disperse phase and the aqueous phase of said emulsion is the continuous phase.

14. A process according to claim 1 wherein said organic compound does not contain any repeating monomeric units.

* * * * *